(12) United States Patent
Arai et al.

(10) Patent No.: US 11,143,621 B2
(45) Date of Patent: Oct. 12, 2021

(54) EDDY CURRENT FLAW DETECTION DEVICE

(71) Applicant: HITACHI ZOSEN CORPORATION, Osaka (JP)

(72) Inventors: Hiroaki Arai, Osaka (JP); Akihiro Shin, Osaka (JP); Takaaki Yamada, Fukuoka (JP); Hiroshi Azuma, Fukuoka (JP)

(73) Assignee: HITACHI ZOSEN CORPORATION, Osaka (JP)

( * ) Notice: Subject to any disclaimer, the term of this patent is extended or adjusted under 35 U.S.C. 154(b) by 79 days.

(21) Appl. No.: 16/650,866

(22) PCT Filed: May 21, 2018

(86) PCT No.: PCT/JP2018/019510
§ 371 (c)(1),
(2) Date: Mar. 26, 2020

(87) PCT Pub. No.: WO2019/064684
PCT Pub. Date: Apr. 4, 2019

(65) Prior Publication Data
US 2020/0292500 A1 Sep. 17, 2020

(30) Foreign Application Priority Data
Sep. 27, 2017 (JP) .............................. JP2017-185534

(51) Int. Cl.
*G01N 27/90* (2021.01)
*G01N 33/207* (2019.01)

(52) U.S. Cl.
CPC ..... *G01N 27/9006* (2013.01); *G01N 27/9046* (2013.01); *G01N 33/207* (2019.01)

(58) Field of Classification Search
CPC .... G01N 27/82; G01N 27/90–27/9026; G01N 27/9046; G01N 27/9093;
(Continued)

(56) References Cited

U.S. PATENT DOCUMENTS 5,130,652 A 7/1992 Kawakami et al.
5,371,463 A * 12/1994 Collins ................ G01N 27/825
324/228
(Continued)

FOREIGN PATENT DOCUMENTS

JP H02147950 6/1990
JP H06331602 12/1994
(Continued)

OTHER PUBLICATIONS

"International Search Report (Form PCT/ISA/210) of PCT/JP2018/019510," dated Jul. 17, 2018, with English translation thereof, pp. 1-4.

*Primary Examiner* — Melissa J Koval
*Assistant Examiner* — Rahul Maini
(74) *Attorney, Agent, or Firm* — JCIPRNET

(57) ABSTRACT

The present invention provides a strong magnetic force and high heat resistance for a magnetic-field forming magnet that applies a magnetic field to a test object to be inspected by an eddy current flaw detection device. A magnetic-field forming magnet for applying a magnetic field to a test object includes a first magnet and a second magnet. The first magnet has a strong magnet force and the second magnet having higher heat resistance than the first magnet is attached to a near end of the first magnet, the end near the test object.

5 Claims, 4 Drawing Sheets

(58) Field of Classification Search
CPC .. G01N 33/20; G01N 33/202; G01N 33/2028; G01N 33/204; G01N 33/2045; G01N 33/207
USPC .......................................... 324/222, 228–243
See application file for complete search history.

(56) References Cited

U.S. PATENT DOCUMENTS

| | | |
|---|---|---|
| 5,414,353 A | 5/1995 | Weischedel |
| 2010/0148766 A1 | 6/2010 | Weischedel |
| 2012/0153944 A1 | 6/2012 | Tada et al. |
| 2014/0049251 A1* | 2/2014 | Peyton ................. G01R 35/005 324/202 |
| 2018/0217097 A1 | 8/2018 | Tada et al. |

FOREIGN PATENT DOCUMENTS

| | | |
|---|---|---|
| JP | H07167674 | 7/1995 |
| JP | 2011047736 | 3/2011 |
| JP | 4885068 | 2/2012 |
| JP | 2017026354 | 2/2017 |
| WO | 0102847 | 1/2001 |

* cited by examiner

EDDY CURRENT FLAW DETECTION DEVICE

CROSS-REFERENCE TO RELATED APPLICATION

This application is a 371 application of the International PCT application serial no. PCT/JP2018/019510, filed on May 21, 2018, which claims the priority benefit of Japan Patent Application No. 2017-185534, filed on Sep. 27, 2017. The entirety of each of the abovementioned patent applications is hereby incorporated by reference herein and made a part of this specification.

TECHNICAL FIELD

The present invention relates to an eddy current flaw detection device and particularly relates to an eddy current flaw detection device using a magnetic saturation method.

BACKGROUND ART

Conventionally, an eddy current flaw detection device described in Patent Literature 1 is used as a flaw detection device for inspecting the presence or absence of a flaw (defect) on the surface of a structure (a subject, a test object) made of a conductive material. The device generates eddy current on a test object and detects the intensity of the eddy current and the change of the shape of eddy current flow, thereby inspecting the presence or absence of a flaw on the test object. If the test object has a flaw, the device can also determine the position, shape, and depth of the flaw.

The inventors examined the case where a plurality of regions have different magnetic permeabilities (heterogeneous magnetic permeability) on the surface of the test object. For example, if the test object is made of a non-ferromagnetic base material and is partially welded, the surface of the test object is basically non-ferromagnetic but a part around a welded point of the test object is magnetized with an uneven magnetic field. In the case where ferromagnetic and non-ferromagnetic regions are mixed on the surface, an inspection conducted by a flaw detection device across the regions may cause noise in an inspection result because of a change in magnetic permeability between the regions. As a solution to the problem of noise, a method of magnetic saturation (magnetic saturation method) is available. In this method, a strong and uniform magnetic field is applied to a test object so as to cancel out an uneven magnetic field generated in an inspection region. The test object is brought into magnetic saturation, that is, a difference in magnetic permeabilities between a ferromagnetic material and a non-ferromagnetic material is substantially eliminated. In the state of magnetic saturation, noise caused by an heterogeneous magnetic permeability on the surface of the test object is considerably reduced. Thus, this method can detect a flaw of the test object even if the surface of the test object has an area containing a ferromagnetic material with an uneven magnetic field.

A magnet is usable for forming such a state of magnetic saturation. A magnet has the property of reducing its magnetic force (demagnetization) with temperature and being completely degaussed at a Curie temperature specific to the magnet. Moreover, a magnet demonstrates the property of not recovering a magnetic force that is reduced at a high temperature even after the magnet is cooled (irreversible demagnetization). Since the formation of the state of magnetic saturation requires a strong magnet, a neodymium magnet with a strong magnetic force may be used. Even if a neodymium magnet has high heat resistance and is usable at a high temperature of 150 degrees, the magnet has a Curie temperature of about 300 degrees centigrade. If an ordinary neodymium magnet reaches 80 degrees or higher, the original magnetic force is not recovered even after the magnet is cooled.

CITATION LIST

Patent Literature

Japanese Patent No. 4885068 is referred to as "Patent Literature 1" in this specification.

SUMMARY OF INVENTION

Technical Problem

If a test object is the exhaust duct of an incineration facility or a canister (metallic cylindrical container) that contains spent nuclear fuel, the surface of the test object has an extremely high temperature. For example, if the surface of the test object reaches 200 degrees centigrade, the magnetic force of the neodymium magnet decreases as the magnet approaches the test object, preventing magnetic saturation on the test object with the neodymium magnet. In order to securely apply a magnetic field to the test object, it is preferable to bring the magnet as close as possible to the test object. If possible, the magnet is to be brought into contact with the test object. However, a neodymium magnet cannot be brought close to or brought into contact with a hot test object.

A heat-resistant magnet has a weak magnetic force. For example, a samarium-cobalt magnet (samarium-cobalt magnet) has a Curie temperature of about 700 to 800 degrees centigrade and thus can be effectively used for practical applications at high temperatures up to about 350 degrees centigrade. However, the magnetic force of a samarium-cobalt magnet is weaker than that of a neodymium magnet and thus a samarium-cobalt magnet cannot achieve sufficient magnetic saturation on the test object.

An object of the present invention is to provide an eddy current flaw detection device including a magnetic-field forming magnet having a strong magnetic force and high heat resistance.

Solution to Problem

An eddy current flaw detection device according to an aspect of the present invention generates eddy current on a test object and inspects a state of the surface of the test object by detecting a change of the eddy current, the eddy current flaw detection device including: a detection part for detecting a change of the eddy current; and a magnetic-field forming magnet that is disposed outside the detection part and applies a magnetic field to the test object, wherein the magnetic-field forming magnet includes a first magnet and a second magnet attached to one end of the first magnet so as to be adjacent to the test object, the second magnet having a higher Curie temperature than the first magnet.

It is preferable that the first magnet includes a neodymium magnet and the second magnet includes a samarium-cobalt magnet.

It is preferable to provide an end cover plate made of a ferromagnetic material, the end cover plate being attached to the other end of the first magnet so as to be remote from the test object.

It is preferable that the second magnet is directed to the surface of the test object at a temperature of 200 degrees centigrade or more.

Furthermore, it is preferable that the test object is a metallic canister that contains spent nuclear fuel, the canister is made of austenitic stainless steel, the canister includes a welded part that is formed by welding austenitic stainless steels, and the eddy current flaw detection device generates eddy current on the welded part and inspects the presence or absence of a flaw on the outer surface of the canister by detecting a change of the eddy current.

Advantageous Effect of Invention

The present invention provides an eddy current flaw detection device including a magnetic-field forming magnet having a strong magnetic force and high heat resistance.

DESCRIPTION OF EMBODIMENT

Figure 1:
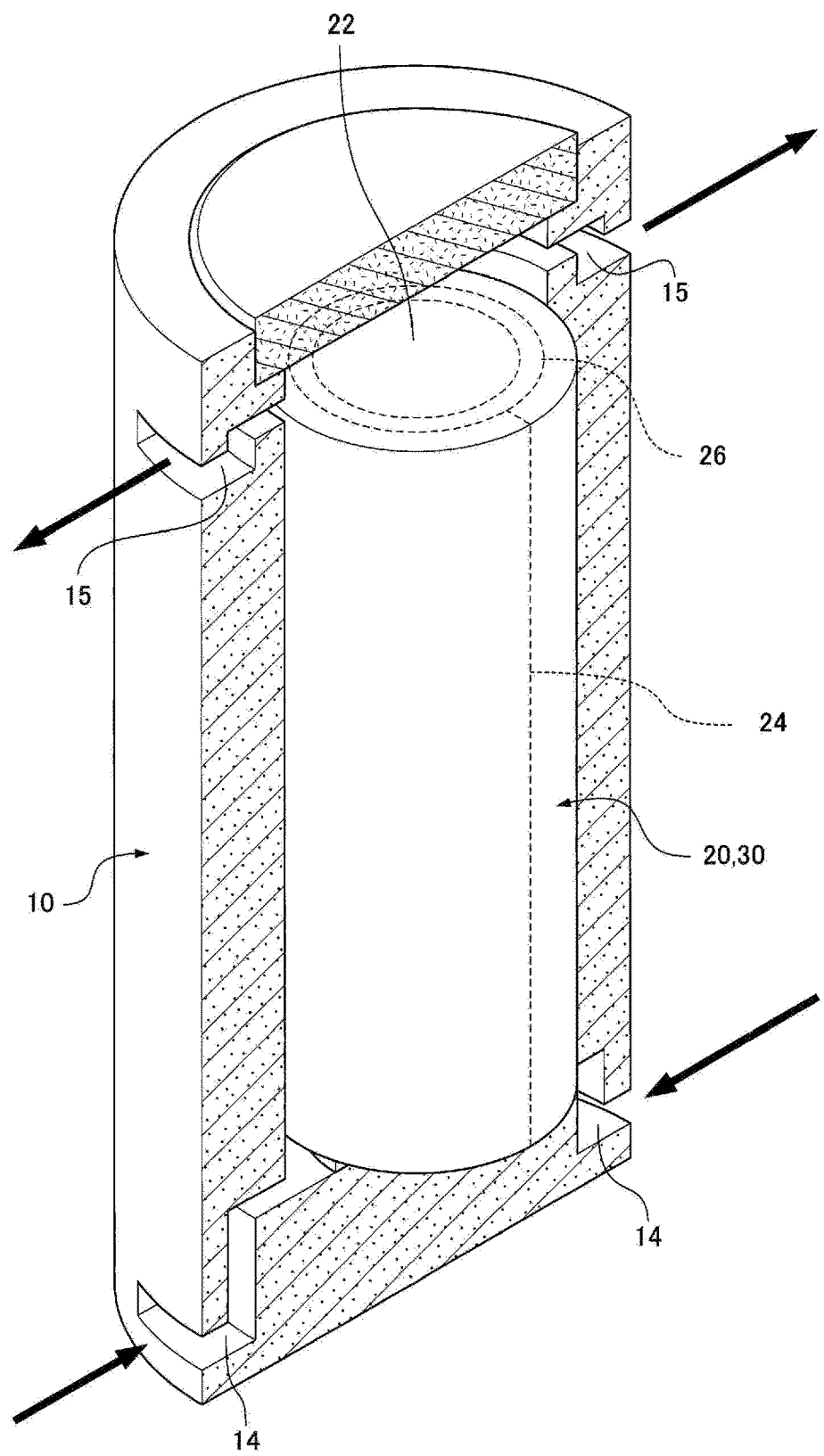
FIG. 1 illustrates a canister to be inspected by an eddy current flaw detection device according to an example of an embodiment of the present invention.

FIG. 1 illustrates a canister 20 (test object) on which a flaw inspection (detection) is conducted by an eddy current flaw detection device according to an example of an embodiment of the present invention. The canister 20 is a metallic cylindrical container that contains spent nuclear fuel. As illustrated in FIG. 1, the canister 20 is stored in a region remote from an urban area, typically in a coastal region while being contained in a large concrete container (concrete cask 10).

In the lower part of the concrete cask 10, an air inlet 14 is provided so as to radially penetrate the concrete cask 10, whereas in the upper part of the concrete cask 10, an air outlet 15 is provided so as to radially penetrate the concrete cask 10. The canister 20 is heated by decay heat from the spent nuclear fuel contained in the canister 20. In the meantime, outside air is drawn from the air inlet 14 and air is discharged from the air outlet 15. In this process, outside air comes into contact with the side of the canister 20, thereby cooling the canister 20.

If the concrete cask 10 is stored in a coastal region, air in the coastal region contains sea salt and thus chloride may rust or corrode the surface of the canister 20 in contact with outside air. Moreover, if a tensile stress is applied to a rusted or corroded point, stress corrosion cracking (SCC) may occur at the point. Thus, the canister 20 is regularly removed from the concrete cask 10 and the presence or absence of SCC is inspected (detected) on the surface of the canister 20.

As illustrated in FIG. 1, the canister 20 includes a cylindrical body with a bottom and a lid 22 closing an opening at the top of the body. The body of the canister 20 and the lid 22 are fixed to each other by welding. As illustrated in FIG. 1, the mark of welding is left as a lid welded part 26. The side of the body of the canister 20 is formed by bending a rectangular metal plate into a cylindrical shape and welding both ends of the metal plate. The mark of welding is also left as a side welded part 24 as illustrated in FIG. 1. The side welded part 24 and the lid welded part 26 are susceptible to a tensile stress and thus SCC is highly likely to occur in the parts. Thus, flaw detection is important particularly on the side welded part 24 and the lid welded part 26.

Figure 2:
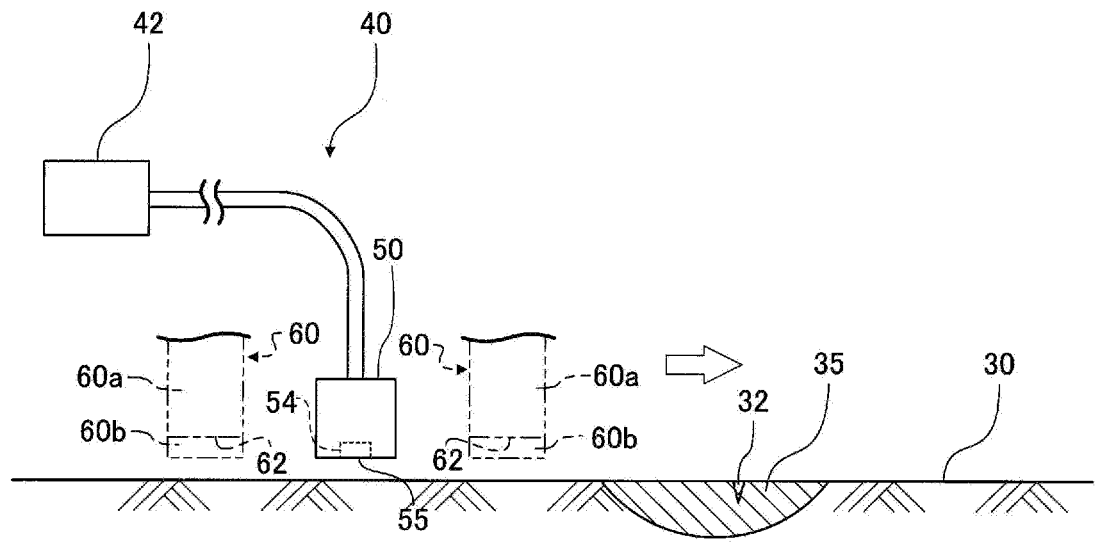
FIG. 2 schematically illustrates an example of the structure of an inspection probe.

FIG. 2 schematically illustrates a state of flaw detection using an eddy current flaw detection device 40. The eddy current flaw detection device 40 includes an inspection probe 50. An alternating magnetic field is generated from the inspection probe 50. When an alternating magnetic field approaches the surface of a test object 30 (e.g., the side wall, lid, and bottom of the canister 20), an eddy current is generated on a metal (typically, austenitic stainless steel in the canister 20) constituting the outer surface of the test object 30. Magnetic flux produced from the eddy current is detected by the inspection probe 50 and a state of the surface of the test object 30 is determined based on a detected magnetic flux density and a waveform.

FIG. 2 schematically illustrates an example of the structure of the eddy current flaw detection device 40. The eddy current flaw detection device 40 includes the inspection probe 50 and a controller 42. The inspection probe 50 includes a detection part 54 for detecting a change of eddy current generated on the surface of the test object 30. The controller 42 has the function of processing a detection signal received from the inspection probe 50.

In this configuration, the lower end face of the detection part 54 is opposed to the surface of the test object 30. The lower end face serves as a detection surface 55 of the inspection probe 50 that receives magnetic flux from eddy current generated on the test object 30.

In this case, the reaction of the surface of the test object 30 with an alternating magnetic field varies depending upon the property of the material of the test object 30. If the material has a uniform property in an inspection range, the eddy current flaw detection device 40 can conduct flaw detection by searching for a part that reacts with an alternating magnetic field in a different manner from other parts. However, if the property of the material, particularly the magnetic permeability of the material varies among positions, a reaction with an alternating magnetic field varies among positions in the absence of a flaw 32. Thus, noise is generated so as to affect an inspection, leading to difficulty in flaw detection. Therefore, it is desirable to remove noise as much as possible.

Figure 3:
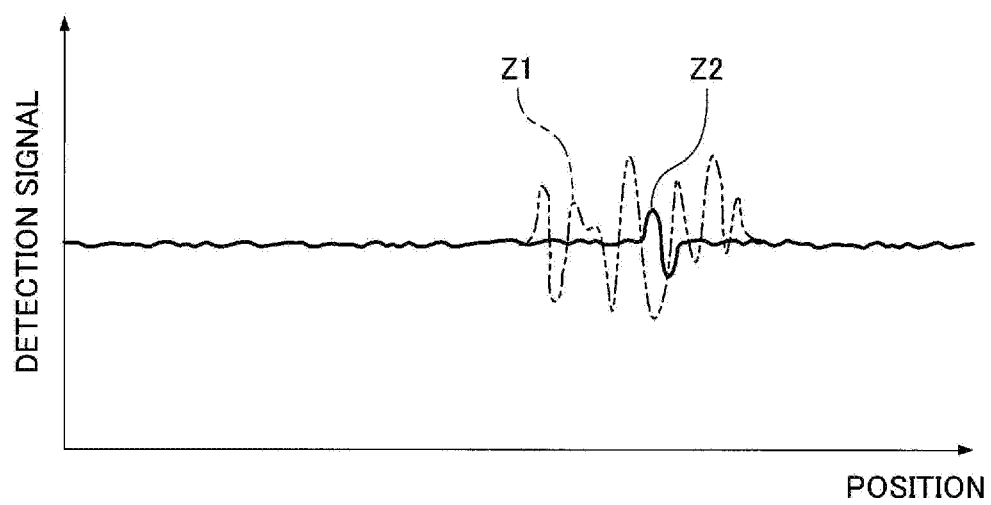
FIG. 3 illustrates a detection signal including noise and a detection signal from which noise is removed.

In FIG. 2, a dissimilar material part 35 that is made of a different material having a different magnetic permeability from an adjacent area appears on a part of the surface of the test object 30. For example, if the test object 30 is the canister 20 illustrated in FIG. 1, a dissimilar material may appear on the side welded part 24 and the lid welded part 26 (welded part). Specifically, if the canister 20 is made of austenitic stainless steel, a ferrite alloy may appear on the welded part. In other words, when austenitic stainless steel is melted in the process of welding, the atomic arrangement of iron (Fe), chromium (Cr), nickel (Ni), molybdenum (Mo), and carbon (C) that constitute the steel is disturbed and thus an alloy having a different atomic arrangement from austenitic stainless steel may appear on the surface of the test object after the completion of welding. In some cases, a ferrite alloy may appear. FIG. 3 indicates a state where noise appears on the detection signal and a state where noise is removed using a magnetic-field forming magnet 60 when the surface of the test object 30 has a heterogeneous magnetic permeability.

The direction of a magnetic field is disturbed at a position where a ferrite alloy is present. Thus, even if the surface has no flaw 32, the detection signal detected by the inspection probe 50 is changed at a position where a ferrite alloy is present. For this reason, in the welded part on which a ferrite alloy appears, it is difficult to determine whether the detection signal is changed by a flaw 32 or a ferrite alloy. Specifically, as illustrated in FIG. 2, if a ferrite alloy appears on the surface of the test object 30 and forms the dissimilar material part 35, the magnetic flux of an alternating magnetic field generated from the inspection probe 50 is disturbed at the position of the dissimilar material part 35. When the inspection probe 50 passes over the position, noise occurs on the detection signal (a graph Z1 in FIG. 3). Thus, even if the dissimilar material part 35 has the flaw 32, it is difficult to detect a change caused by the flaw 32 on the detection signal.

As indicated by virtual lines in FIG. 2, the magnetic-field forming magnet 60 is disposed outside the inspection probe 50, so that the magnetic permeabilities of the test object 30 and the dissimilar material part 35 are changed when a magnetic field is received from the magnetic-field forming magnet 60. By properly setting the intensity of a magnetic field of the magnetic-field forming magnet 60, the test object 30 and the dissimilar material part 35 have substantially equal magnetic permeabilities. Thus, a reaction with an alternating magnetic field from the inspection probe 50 is substantially the same in the dissimilar material part 35 and other parts, so that the detection signal is intensified only at the position of the flaw 32 (a graph Z2 in FIG. 3).

In this way, a strong magnetic field is applied to the test object 30 by the magnetic-field forming magnet 60, so that a change (noise) of the detection signal by a ferrite alloy is removed with significance as indicated by graph Z2 of FIG. 3. However, if the test object 30 is the canister 20 containing spent nuclear fuel as illustrated in FIG. 1, the surface of the canister 20 reaches quite a high temperature (typically 200 degrees centigrade or higher) and thus the magnetic-field forming magnet 60 needs to be resistant to such a high temperature. As has been discussed, however, a magnet having a strong magnetic force is typically less resistant to heat, whereas a heat-resistant magnet typically has a weak magnetic force.

Figure 4:
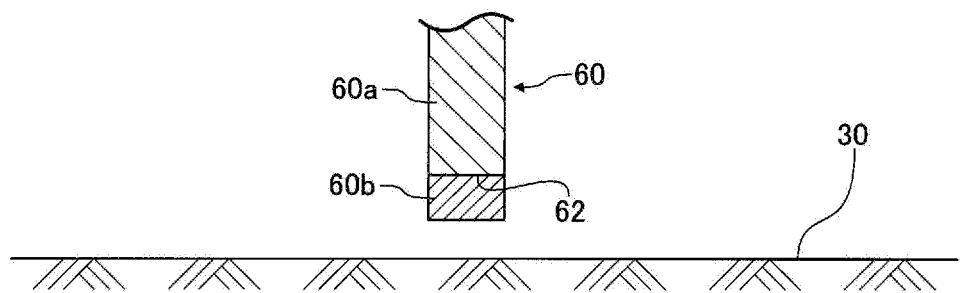
FIG. 4 illustrates the structure of a magnetic-field forming magnet.

As illustrated in FIG. 4, the magnetic-field forming magnet 60 in the present embodiment includes a first magnet 60a and a second magnet 60b. The first magnet 60a has a stronger magnetic force than the second magnet 60b and the second magnet 60b is more resistant to heat than the first magnet 60a. In a specific example, the first magnet 60a is a neodymium magnet and the second magnet 60b is a samarium-cobalt magnet.

In this case, heat resistance means an upper temperature limit during heating when a heated magnet is kept in irreversible demagnetization even after being cooled. Generally, a material having a high Curie temperature is highly resistant to heat.

The second magnet 60b is attached to one end of the first magnet 60a, the end having a magnetic pole. As illustrated in FIG. 4, the end to which the second magnet 60b is attached is a near end 62 of the first magnet 60a (the end near the test object 30), the near end 62 being directed toward the test object 30. The second magnet 60b is attached to the magnetic pole of the first magnet 60a, so that the first magnet 60a and the second magnet 60b are fixed to each other with a magnetic force.

In the case of the series connection of the two magnets, the magnetic force of the overall magnetic-field forming magnet 60 is not simply equal to the sum of the magnetic forces of the two magnets. If the first magnet 60a and the second magnet 60b have different magnetic forces according to the present embodiment, the magnetic force of the overall magnet lies about halfway between the first magnet 60a and the second magnet 60b. As a specific example, it is assumed that the first magnet 60a is a neodymium magnet having a surface magnetic-flux density of 500 mT. Furthermore, it is assumed that the second magnet 60b is a samarium-cobalt magnet having a surface magnetic-flux density of 300 mT. In this case, the magnetic pole (the lower end of the second magnet 60b in FIG. 4) of the overall magnetic-field forming magnet 60 has a surface magnetic-flux density of about 450 mT. Hence, the magnetic force of the overall magnetic-field forming magnet 60 is greater than that of the second magnet 60b.

Since the second magnet 60b is attached to the near end 62 of the first magnet 60a, heat from the test object 30 at a high temperature is directly received by the high heat-resistant second magnet 60b. Thus, the ability of the overall magnetic-field forming magnet 60 to generate a magnetic field is not reduced even if the first magnet 60a has low heat resistance. Specifically, even if the canister 20 serving as the test object 30 as illustrated in FIG. 1 has a surface temperature of about 200 degrees centigrade, heat from the canister 20 does not reduce the magnetic force of the second magnet 60b as long as the second magnet 60b is a samarium-cobalt magnet that is practically resistant to heat up to 350 degrees centigrade. If heat from the surface of the canister 20 is not transmitted to the first magnet 60a (e.g., a neodymium magnet), the magnetic force of the overall magnetic-field forming magnet 60 does not decrease.

Figure 5:
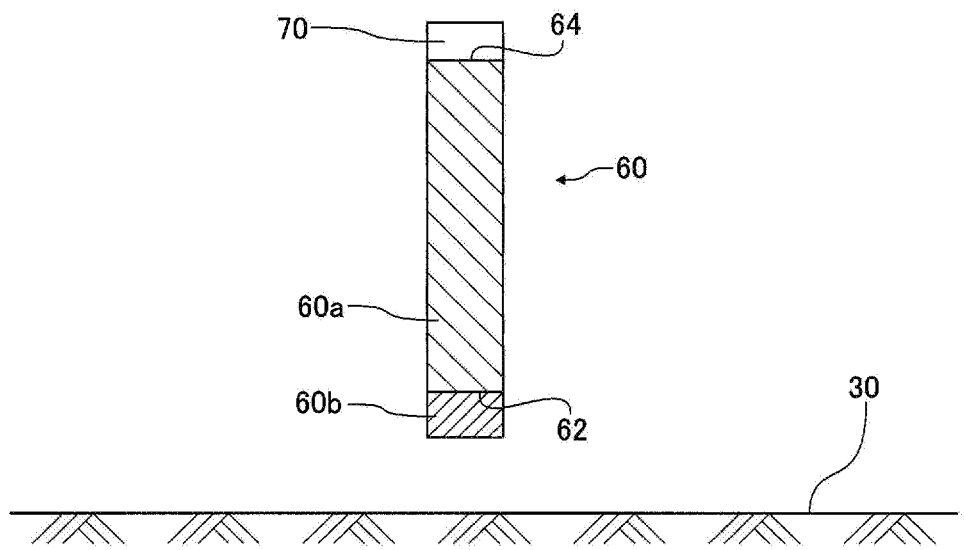
FIG. 5 illustrates that an end cover plate is attached to the magnetic-field forming magnet.

If the first magnet 60a is a rod-shaped magnet as illustrated in FIG. 5, an end cover plate 70 may be attached to one end of the first magnet 60a. The end cover plate 70 is attached over one end of the first magnet 60a, that is, a far end 64 located at a distance from the test object 30 (the end remote from the test object) on the opposite side from the near end 62. This configuration reduces magnetic fluxes from the side of the far end 64 and increases a magnetic flux density on the surface of the near end 62.

Figure 6:
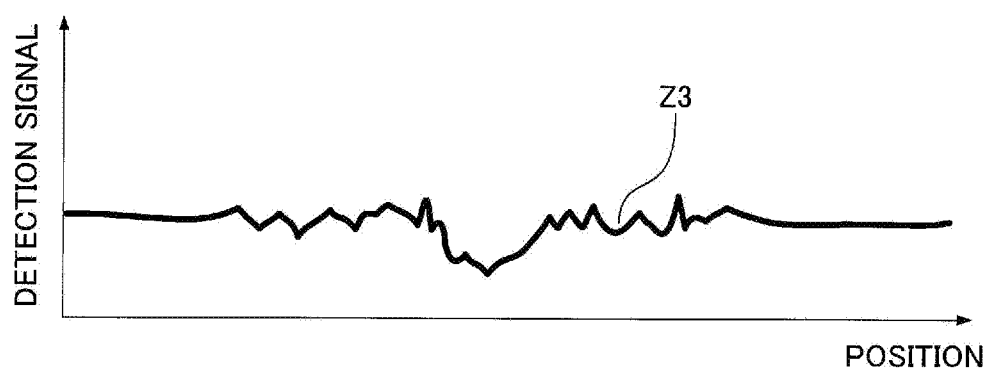
FIG. 6 is a graph of a detection signal including noise.
Figure 7:
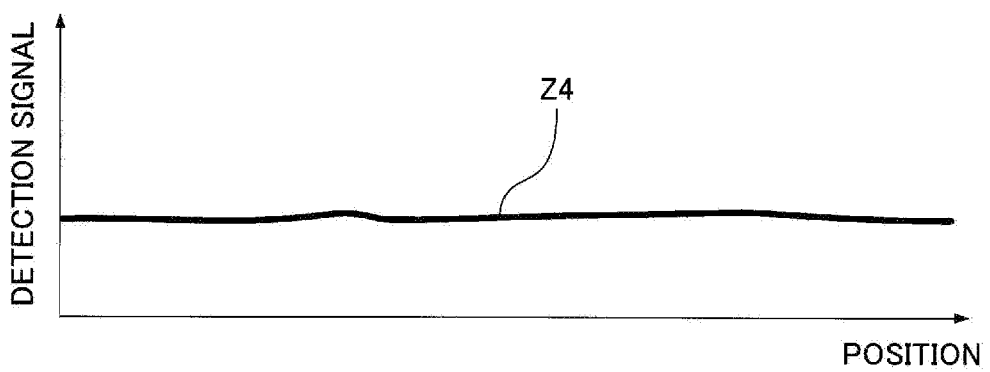
FIG. 7 is a graph of a detection signal from which noise is removed.

Referring to FIGS. 6 and 7, it will be described that noise is sufficiently removed by using the magnetic-field forming magnet 60 that is a combination of the first magnet 60a and the second magnet 60b as in FIG. 4. Graphs in FIGS. 6 and 7 indicate the detection signal in the detection of the eddy current flaw detection device 40 on the welded part (the side welded part 24 or the lid welded part 26) of the canister 20 in FIG. 1. Specifically, the inventors inspected the surface of a welded specimen of austenitic stainless steel, a material of the canister 20, and then examined the obtained detection signal. More specifically, specimens of SUS316 were TIG welded together and then the welded part was inspected. Graphs indicate the detection signal obtained when the surface is unflawed.

In FIGS. 6 and 7, the test object was inspected under the same conditions. Graph Z3 in FIG. 6 shows the detection signal obtained when the magnetic-field forming magnet 60 only includes a samarium-cobalt magnet. As indicated by a graph Z3, even if the surface of the specimen is not flawed, many fluctuations appear and noise occurs in the detection signal due to the influence of a dissimilar metal (e.g., a ferrite alloy) appearing on the welded part. The noise is not sufficiently removed only by the samarium-cobalt magnet.

Graph Z4 in FIG. 7 shows the detection signal obtained when the magnetic-field forming magnet 60 is a combination of the first magnet 60a (neodymium magnet) and the second magnet 60b (samarium-cobalt magnet) as illustrated in FIG. 4. Graph Z4 in FIG. 7 is obviously flatter than graph Z3 in FIG. 6, proving that noise is sufficiently removed by the combination of the neodymium magnet and the samarium-cobalt magnet.

As has been discussed, in the present embodiment, the magnetic-field forming magnet 60 is not damaged by heat even when approaching the hot test object 30. Furthermore, noise is sufficiently removed. This achieves a proper inspection on the presence or absence of a flaw on the outer surface of a welded part of a canister for spent nuclear fuel, the canister being made of austenitic stainless steel.

In the present embodiment, the canister 20 in FIG. 1 particularly serves as the test object 30 made of austenitic stainless steel. The test object 30 is not limited to the canister 20. The eddy current flaw detection device 40 can be used for flaw detection of all materials on which eddy current may occur.

The specific configuration of the detection part 54 of the eddy current flaw detection device 40 may be changed in various ways as long as a change of eddy current generated on the surface of the test object 30 can be detected. For example, uniform eddy current may be generated by a large exciting coil and a change of eddy current may be detected by a small detecting coil that is disposed below the exciting coil and has the central axis orthogonal to the exciting coil. Alternatively, two detecting coils may be disposed with an exciting coil interposed therebetween and a current difference between the two detecting coils may be measured as a detection signal. Additionally, a change of impedance may be measured to allow a single coil to act as both of an exciting coil and a detecting coil.

In the present embodiment, the second magnet 60b is fixed to the first magnet 60a with a magnetic force, thereby eliminating the need for another member for fixing the first magnet 60a and the second magnet 60b. However, if it is necessary to prevent a misalignment between the first magnet 60a and the second magnet 60b when the magnetic-field forming magnet 60 receives an external impact, adhesive (e.g., two-pack type epoxy adhesive) suitable for bonding metals may be applied between the first magnet 60a and the second magnet 60b. Alternatively, a tapped hole may be provided from the second magnet 60b to the first magnet 60a such that the first magnet 60a and the second magnet 60b are firmly coupled to each other with a bolt screwed into the tapped hole. In order to prevent a misalignment between the first magnet 60a and the second magnet 60b, a cover provided over the first magnet 60a and the second magnet 60b may be provided over the magnetic-field forming magnet 60.

REFERENCE SIGNS LIST 10 concrete cask
20 canister
30 test object
40 eddy current flaw detection device
50 inspection probe
60 magnetic-field forming magnet
62 near end
64 far end
70 end cover plate

The invention claimed is:

1. An eddy current flaw detection device that generates eddy current on a test object and inspects a state of a surface of the test object by detecting a change of the eddy current, the eddy current flaw detection device comprising:
a detection part for detecting the change of the eddy current; and
a magnetic-field forming magnet that is disposed outside the detection part and applies a magnetic field to the test object,
wherein the magnetic-field forming magnet includes:
a first magnet, and a second magnet attached to one end of the first magnet so as to be adjacent to the test object, and
the second magnet has a Curie temperature higher than a Curie temperature of the first magnet.

2. The eddy current flaw detection device according to claim 1, wherein the first magnet includes a neodymium magnet, and
the second magnet includes a samarium-cobalt magnet.

3. The eddy current flaw detection device according to claim 1, further comprising an end cover plate made of a ferromagnetic material, the end cover plate being attached to the other end of the first magnet so as to be remote from the test object.

4. The eddy current flaw detection device according to claim 1, wherein the second magnet is directed to the surface of the test object, which is at a temperature of 200 degrees centigrade or more.

5. The eddy current flaw detection device according to claim 1, wherein the test object is a metallic canister that contains spent nuclear fuel,
the canister is made of austenitic stainless steel,
the canister includes a welded part that is formed by welding austenitic stainless steels, and
the eddy current flaw detection device generates eddy current on the welded part and inspects presence or absence of a flaw on an outer surface of the canister by detecting the change of the eddy current.

* * * * *